United States Patent [19]

Rizzi

[11] 3,932,678
[45] Jan. 13, 1976

[54] NOVEL DIHYDROCHALCONE SWEETENER COMPOSITIONS

[75] Inventor: George P. Rizzi, Springfield Township, Hamilton County, Ohio

[73] Assignee: The Procter & Gamble Company, Cincinnati, Ohio

[22] Filed: June 25, 1974

[21] Appl. No.: 482,963

Related U.S. Application Data

[62] Division of Ser. No. 157,682, June 28, 1971, Pat. No. 3,855,301.

[52] U.S. Cl. ................. 426/548; 426/601; 426/658
[51] Int. Cl.² .......................................... A23L 1/236
[58] Field of Search ........... 426/217, 213, 548, 601, 426/658; 260/590

[56] References Cited
UNITED STATES PATENTS

| 3,087,821 | 4/1963 | Horowitz et al. | 426/217 |
| 3,739,064 | 6/1973 | Rizzi | 426/217 |
| 3,743,716 | 7/1973 | Rizzi | 424/49 |
| 3,751,270 | 8/1973 | Rizzi | 423/380 |

OTHER PUBLICATIONS

Inglett et al; J. of Food Science, Vol. 34, 1969, pp. 101–103.

Primary Examiner—Norman Yudkoff
Assistant Examiner—Curtis P. Ribando
Attorney, Agent, or Firm—Jerry J. Yetter; Julius P. Filcik; Richard C. Witte

[57] ABSTRACT

A novel artificial sweetener compound, 3-(m-hydroxyphenyl)phloropropiophenone and a process for preparing same, as well as other 3-arylphloropropiophenones, from aryl aldehydes and phloroglucinol.

9 Claims, No Drawings

NOVEL DIHYDROCHALCONE SWEETENER COMPOSITIONS

This is a division of application Ser. No. 157,682, filed June 28, 1971, now U.S. Pat. No. 3,855,301.

BACKGROUND OF THE INVENTION

This invention relates to artificial sweetener compounds and compositions and to a process for preparing same. The novel sweetener compound, 3-(m-hydroxyphenyl)phloropropiophenone, is disclosed.

Hesperetin dihydrochalcone, and alkyl homologs thereof, have been previously suggested for use as artificial sweeteners; see the copending applications of Rizzi, entitled "Dihydrochalcone Sweetening Agent", Ser. No. 76,972, filed Sept. 30, 1970; "Improved Sugar Compositions", Ser. No. 76,974, filed Sept. 30, 1970; and Rizzi and Neely, "Sweetening Compositions", Ser. No. 76,973, filed Sept. 30, 1970.

Heretofore, the preparation of arylphloropropiophenone sweeteners, such as hesperetin dihydrochalcone and its alkyl homologs, has been carried out by using various naturally-occurring precursor materials such as homoneohesperetin and various flavonone glycosides (see the foregoing references). Such naturally-occurring precursor materials are known to be expensive and available only in limited quantities. Furthermore, the use of naturally-occurring precursor materials does not provide a method for synthesizing useful 3-arylphloropropiophenones not found in nature, e.g., the novel artificial sweetener compound, 3-(m-hydroxyphenyl)phloropropiophenone, disclosed herein. For these reasons, it is desirable to provide a process for preparing 3-arylphloropropiophenones, such as hesperetin dihydrochalcone and analogs thereof, which does not require the use of naturally-occurring precursor materials.

Zemplin and Bognar, Chem. Ber., 75, 1043 (1942) disclose a method for preparing hesperetin dihydrochalcone using glycoside intermediates. While this procedure does yield the desired hesperetin dihydrochalcone reaction products, it is far too complex for use on an industrial scale.

It is an object of this invention to provide a novel 3-arylphloropropiophenone compound, 3-(m-hydroxyphenyl)phloropropiophenone, and sweetener compositions containing same. It is a further object herein to provide a process for preparing 3-arylphloropropiophenones, such as hesperetin dihydrochalcone, and certain analogs and homologs thereof, which does not require the use of naturally-occurring precursor materials. These and other objects are obtained by this invention as will be seen from the following disclosure.

SUMMARY OF THE INVENTION

The present invention relates to the novel compound 3-(m-hydroxyphenyl)phloropropiophenone,

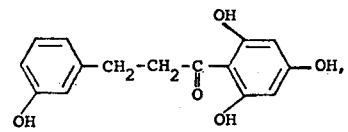

a process for its preparation, and sweetener compositions containing same.

The present invention also encompasses a general process for preparing 3-arylphloropropiophenones, e.g., hesperetin dihydrochalcone, and certain homologs and analogs thereof, comprising: (1) heating an aromatic aldehyde of the type hereinafter disclosed with cyanoacetic acid in the presence of certain catalysts to form α-cyanocinnamic acid derivatives; (2) reducing the α-cyanocinnamic acid derivatives prepared in Step (1) (e.g., with a sodium-mercury (Na/Hg) amalgam at room temperature) to provide the corresponding α-cyano-β-arylpropionic acid; (3) decarboxylating the α-cyano-β-arylpropionic acid prepared in Step (2) by heating (e.g., in the presence of an organic base such as quinoline) to form the corresponding β-arylpropionitrile; (4) condensing the β-arylpropionitrile prepared in Step (3) with phloroglucinol in the presence of a mild Lewis acid (e.g., zinc chloride) to form a phloroglucinol condensate in the immonium salt form; and (5) boiling the immonium salt prepared in Step (4) in water to provide the desired 3-arylphloropropiophenone compound.

DETAILED DESCRIPTION OF THE INVENTION

The reaction sequence involved herein is as follows:

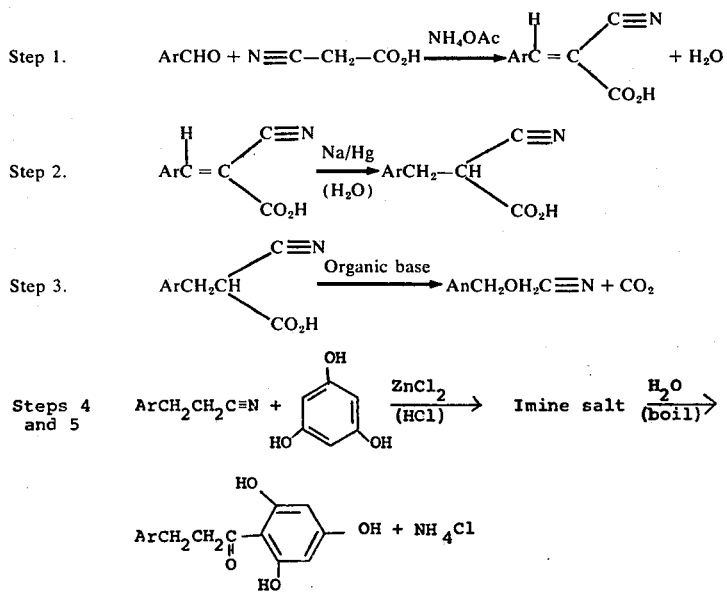

wherein Ar is 3-hydroxy-4-alkoxyphenyl, wherein alkoxy includes methoxy, ethoxy, propoxy, butoxy and the like. Likewise, Ar can be other aryl substituents including phenyl, 3,4-methylenedioxyphenyl, 4-hydroxyphenyl, and the like. A preferred aldehyde compound herein has 3-hydroxy-4-methoxyphenyl as the aryl group, Ar, since this yields hesperetin dihydrochalcone, directly. Also preferred are the other aldehydes wherein Ar is 3-hydroxy-4-alkoxyphenyl, since these yield sweet alkyl homologs of hesperetin dihydrochalcone. When Ar is 3-hydroxyphenyl, the novel sweetener compound 3-(m-hydroxyphenyl)phloropropiophenone is secured.

Step (1) of the present process involves the catalytic condensation of an aromatic aldehyde of the type hereinabove disclosed with cyanoacetic acid to form $\alpha$-cyanocinnamic acid derivatives. This initial reaction can be catalyzed by acids or bases, e.g., 0.1 molar hydrochloric acid, 0.1 molar sodium hydroxide, 0.1 molar pyridine or piperidine and the like. An especially preferred catalyst herein is ammonium acetate, which is disclosed for use in condensing cyclic aldehydes with cyanoacetic acid in Organic Syntheses, Coll. Vol. 4, 234. While a solvent is not necessary in this condensation step, a non-polar, water-immiscible organic solvent is preferably employed. The liquid hydrocarbons, e.g., hexane, petroleum ether, light mineral oil, and the like are suitable solvents, as are liquid aromatic solvents, including benzene, xylene, and toluene. Solvents capable of forming azeotropes with water, especially benzene and xylene, are preferred in Step (1) of the present process since water can then be removed from the reaction mixture by azeotropic distillation. Step (1) herein is usually carried out at a temperature from 0°C to 200°C, preferably 85°C to 150°C to minimize product decomposition and to insure removal of the water which is formed.

Step (2) of the process involves the reduction of the $\alpha$-cyanocinnamic acid prepared in Step (1) by means of any of the well-known reduction procedures. For example, the use of alkali metals in combination with methanol and ethanol, the use of the complex metal hydrides, e.g., sodium borohydride, hydrogen gas in the presence of platinum oxide, or by means of the sodium-mercury amalgams. A preferred reducing agent herein is a sodium-mercury amalgam (2% sodium). Suitable solvents in this step include water and aqueous alcohol solvents; water is preferred. The reduction Step (2) can be carried out at a temperature from about 30°C to about 100°C, preferably about 50°C, to maintain a reasonable reduction rate, in the manner more fully disclosed by McRae and Vinning, Can. J. Res., 6, 409 (1932).

Step (3) herein involves the decarboxylation of the $\alpha$-cyano-$\beta$-arylpropionic acid prepared in Step (2). This decarboxylation can be effected by heat (ca. 200°C). However, the decarboxylation of the $\alpha$-cyano-$\beta$-arylpropionic acids is preferably catalyzed by means of an organic base such as quinoline, pyridine, triazine, 8-hydroxyquinoline and the like. Excess organic base can be used as a solvent in the decarboxylation Step (3), or the reaction can be done without solvent. The base-catalyzed decarboxylation, which is preferred, is carried out by heating the $\alpha$-cyano-$\beta$-arylpropionic acid in the presence of the organic base (at least 0.1 mole base:1 mole acid) at a temperature from about 125°C to 175°C. The decarboxylation is readily effected in from about 10 minutes to about one hour of heating for each mole of $\alpha$-cyano-$\beta$-arylpropionic acid being decarboxylated.

Steps (4) and (5) herein involve the condensation of the $\beta$-arylpropionitrile formed in Step (3) with phloroglucinol in the presence of a mild Lewis acid and a gaseous hydrogen halide, e.g., HCl, in the manner of Johnston, U.S. Pat. No. 2,789,995 (Apr. 23, 1957), incorporated herein by reference. Following the condensation, the resulting immonium salt is hydrolyzed by boiling with water. Suitable Lewis acids herein include, for example, zinc chloride, titanium tetrachloride, zinc bromide, titanium trichloride, mercuric chloride and the like. While any of the common Lewis acids can be employed in the condensation Step (4), zinc chloride is especially preferred for this use. The condensation with phloroglucinol can be carried out at a low temperature, i.e., from about −10°C to about 30°C, preferably about 0°C to 10°C to control the rapid rate; an anhydrous, aprotic solvent such as diethyl ether or diglyme is used.

Reaction of the $\beta$-arylpropionitriles with phloroglucinol in the presence of the Lewis acid results in the formation of the immonium salt of the phloroglucinol-$\beta$-arylpropionitrile condensate. This reaction product is not isolated herein, but is hydrolyzed directly. This hydrolysis, with loss of ammonium chloride, is effected by adding at least one mole of water per mole of immonium salt to the reaction mixture from Step (4) and boiling the mixture. This hydrolysis usually requires from about 5 minutes to about one hour of boiling per mole of salt being decomposed. The 3-arylphloropropiophenone product is recovered by crystallization.

In a preferred mode, the process herein is carried out by admixing an aryl aldehyde of the type hereinabove disclosed with cyanoacetic acid (1:1 mole basis) in the presence of a catalytic amount (ca. 0.1 mole equivalent) of ammonium acetate in sufficient benzene solvent to dissolve the reactants. The reaction mixture is heated in a vessel fitted with a distilling head and water and benzene are removed as an azeotrope. Following removal of all the formed water, the $\alpha$-cyanocinnamic acid derivative of the aryl aldehyde is recovered by filtration. The $\alpha$-cyanocinnamic acid aldehyde derivative is then suspended in water and stirred while about 1 equivalent of sodium-mercury amalgam is added portionwise. The temperature is maintained at about 30°C to 50°C by the rate of amalgam addition. The water-soluble salt of the corresponding $\alpha$-cyano-$\beta$-arylpropionic acid is formed. The reaction mixture is decanted from the residual mercury, acidified and extracted with ether. The $\alpha$-cyano-$\beta$-arylpropionic acid is recovered from the ether and admixed with at least 0.1 molar equivalent of quinoline and heated at about 150°C for about one hour, until carbon dioxide evolution ceases. The quinoline is removed by HCl extraction and the resulting $\beta$-arylpropionitrile is dissolved in diethyl ether solvent. Phloroglucinol (1 mol. eq.) and zinc chloride (0.1 mol. eq.) are added and the mixture is cooled to about 0°C and HCl gas is passed through the mixture. The oily product separates and crystallizes; the ether is decanted. Water is added to the residue and boiled about 1 hour. The resulting oil crystallizes and is filtered and recrystallized (H$_2$O/ethanol) to yield the 3-arylphloropropiophenone.

The following examples serve to illustrate the preparation of 3-(m-hydroxyphenyl)phloropropiophenone and hesperetin dihydrochalcone and analogs thereof by the present process, but are not intended to be limiting thereof. The aromatic aldehydes used in the examples are commercially available.

EXAMPLE I

Preparation of 3-(m-Hydroxyphenyl)phloropropiophenone

Step 1. α-Cyano-m-hydroxycinnamic acid.

A 300 ml. round bottom flask equipped with a mechanical stirrer, Y-adapter, Dean-Stark water separator, cold water condenser, and $N_2$ inlet was charged with m-hydroxybenzaldehyde (26.84 g.), cyanoacetic acid (17.4 g.), ammonium acetate (2 g.) and benzene (200 ml.). The mixture was stirred and vigorously refluxed for 2.0 hr. during which time nearly 1 molar equivalent of water was collected. An electrically heated oil bath (ca. 110°C) was used for heating. After cooling to room temperature, the reaction product was separated by suction filtration, washed with benzene, and air dried to yield 38.0 g. (100%) of a granular, bright yellow solid. The crude product, which still contained a small amount of ammonium acetate, was entirely suitable for direct reduction via sodium amalgam (see below). After recrystallization from boiling water the pure compound was obtained having a m.p. of 225°–227°C.

Step 2. Sodium Amalgam Reduction.

A 500 ml. three-neck round bottom flask equipped with a mechanical stirrer was charged with 25 g. of crude α-cyano-m-hydroxycinnamic acid (above) and 100 ml. of water. The slurry was stirred vigorously while 250 g. of freshly prepared 2.5% sodium amalgam was added. The amalgam was added in roughly 50 g. portions at five minute intervals while the reaction temperature was maintained at about 30°–40°C (water bath). As the reaction proceeded, the yellow solid dissolved and ultimately (~30 min.) a clear, nearly colorless solution was produced. After stirring 1 hour, the solution was decanted from the residue of Hg, cooled in an ice bath and acidified to pH 2 with 6N HCl. Extraction with diethyl ether followed by brine washing, $Na_2SO_4$ drying, and concentration of the ether solution yielded 21.7 g. of a clear brown oil which rapidly crystallized at room temperature. NMR analysis indicated that a quantitative yield of the desired dihydrocinnamic acid had been obtained. The product was of sufficient purity to be used in the decarboxylation step described below.

Step 3. Decarboxylation.

A 300 ml. flask equipped with a magnetic stirrer, cold water condenser, $CO_2$ outlet and bubbler, and a heated oil bath was charged with 21 g. of crude α-cyano-m-hydroxydihydrocinnamic acid (above) and freshly redistilled quinoline (10 ml.). The acid underwent smooth decarboxylation at an oil bath temperature of 150°C with $CO_2$ evolution ceasing after about 2.5 hr. For workup, the cooled mixture was treated with 200 ml. of 5N HCl and extracted thoroughly with several portions of diethyl ether totalling 350 ml. The ether was washed with water (1 × 100 ml.), saturated $NaHCO_3$ (4 × 50 ml.), brine (1 × 100 ml.), and dried over anhydrous $Na_2SO_4$. Concentration of the ether solution gave 11.15 g. (69% yield) of β-(m-hydroxyphenyl)propionitrile as a pale yellow solid. Recrystallization from ethyl acetate/hexane gave the pure compound as light yellow crystals, m.p. 64°–66°C.

Steps 4 and 5. Condensation with phloroglucinol and hydrolysis.

A 100 ml. pear shaped flask equipped with a delivery tube so arranged that gas could be bubbled through the reaction mixture was charged with 1.764 g. of β-(m-hydroxyphenyl)propionitrile (above), anhydrous phloroglucinol (1.533 g.; commercial) and anhydrous diethyl ether (60 ml.). After the reactants were completely dissolved by gentle swirling at room temperature, 0.5 g. of anhydrous (fused) zinc chloride was added, the delivery tube was attached, and the mixture was cooled to 0°–5°C in an ice bath. HCl gas was then passed through the mixture at a vigorous rate for 1.75 hours. As the gas passed through the cold solution, the reaction product separated in the form of a viscous oil adhering to the walls of the flask. The mixture was then stored at 0°C, protected from moisture, during which time the oily product partially crystallized (16 hrs.). The supernatant ether solution was decanted and the residual semi-solid mass was boiled with 50 ml. of water under reflux for 2 hours. On cooling, an oil separated which rapidly crystallized. The solid was filtered at 0°C, washed with ice water, and dried under vacuum to yield 1.15 g. (35%) of 3-(m-hydroxyphenyl)phloropropiophenone. Recrystallization from 2:1 $H_2O$/EtOH gave 0.8 g. analytically pure material, m.p. 231.5°–234°C. The infrared and nmr spectra of this material were consistent with the proposed structure. Anal.: Calculated for $C_{15}H_{14}O_5$ C, 65.69; H, 5.15; Found: C, 65.38; H, 5.36.

In the above procedure the quinoline used in the decarboxylation Step (3) is replaced by an equivalent amount of pyridine and triazine, respectively, and equivalent results are secured. Using the same procedure, the organic base is deleted and the temperature is increased to ca. 210°C and decarboxylation occurs in equivalent fashion.

EXAMPLE II

Preparation of Hesperetin Dihydrochalcone

Step 1. α-Cyano-3-hydroxy-4-methoxycinnamic acid.

A 1000 ml. 1-neck round bottom flask equipped with a mechanical stirrer, Y-adapter, Dean-Stark water separator, cold water condenser, and $N_2$ inlet was charged with isovanillin (83.5 g.), tech. grade cyanoacetic acid (43.0 g.), ammonium acetate (5 g.) and benzene (500 ml.). The mixture was stirred and vigorously refluxed for 2.25 hours during which time nearly 10 ml. of water collected. An electrically heated oil bath (ca. 110°C) was used for heating. After cooling to room temperature the reaction product was separated by suction filtration, washed with benzene, and air dried to yield 113.5 g. (100%) of a granular, bright yellow solid. The crude product, which still contained a small amount of ammonium acetate was entirely suitable for direct reduction via sodium amalgam (below). After recrystallization from boiling water, the pure compound was obtained having a m.p. of 280°–282°C.

Step 2. Sodium Amalgam Reduction.

A 500 ml. three-neck round bottom flask equipped with a mechanical stirrer was charged with 20 g. of crude α-cyano-3-hydroxy-4-methoxycinnamic acid (above) and 100 ml. of water. The slurry was stirred vigorously while 250 g. of freshly prepared 2.5% sodium amalgam was added. The amalgam was added in roughly 50 g. portions at five minute intervals while the reaction temperature was maintained at about 30°–40°C (water bath). As the reaction proceeded, the yellow solid dissolved and ultimately (~30 min.) a clear, nearly colorless solution was produced. After stirring 1 hour, the solution was decanted from the residue of Hg, cooled in an ice bath and acidified to pH 2 with 6N HCl. Extraction with diethyl ether, followed by brine washing, $Na_2SO_4$ drying, and concentration of the ether solution yielded 20 g. of a clear brown oil which rapidly crystallized completely at room temperature. NMR analysis indicated that a quantitative yield of the desired dihydrocinnamic acid had been obtained. The product was of sufficient purity to be used in the decarboxylation step described below.

Step 3. Decarboxylation.

A 100 ml. round bottom flask equipped with a magnetic stirrer, cold water condenser, $CO_2$ outlet and bubbler, and a heated oil bath was charged with 14.9 g. of crude α-cyano-3-hydroxy-4-methoxydihydrocinnamic acid (above) and freshly redistilled quinoline (8 ml.). The acid underwent smooth decarboxylation at an oil bath temperature of 150°–155°C with $CO_2$ evolution continuing 45 min. The mixture was then heated 1 hour at 165°C (oil bath) and permitted to cool to room temperature. For workup, the cooled mixture was treated with 500 ml. of 1N HCl and extracted thoroughly with several portions of ether totalling 350 ml. The ether was washed with water (1 × 100 ml.), saturated $NaHCO_3$ (4 × 50 ml.), brine (1 × 100 ml.), and finally dried over anhydrous $Na_2SO_4$. Concentration of the ether solution gave 8.3 g. (70% yield) of β-(3-hydroxy-4-methoxyphenyl)propionitrile as a pale yellow solid. Recrystallization from ethyl acetate/hexane gave the pure compound as light yellow crystals, m.p. 82°C (62% yield of recrystallized product).

Steps 4 and 5. Condensation with Phloroglucinol and Hydrolysis.

A 100 ml. pear shaped flask equipped with a delivery tube so arranged that gas could be bubbled through the reaction mixture was charged with 2.131 g. β-(3-hydroxy-4-methoxyphenyl)propionitrile (above), anhydrous phloroglucinol (1.533 g.; commercial), and anhydrous diethyl ether (60 ml.). After the reactants were completely dissolved by gentle swirling at room temperature, 0.5 g. of anhydrous (fused) zinc chloride was added, the delivery tube was attached, and the mixture was cooled to 0°–5°C in an ice bath. HCl gas was then passed through the mixture at a vigorous rate for 2 hours. As the gas passed through the cold solution, the reaction product separated in the form of a viscous oil adhering to the walls of the flask. The mixture was then stored at 0°C, protected from moisture, during which time the oily product partially crystallized (~16 hrs.). The supernatant ether solution was decanted and the residual semi-solid mass was boiled with 25 ml. of water under reflux for 1.5 hour. On cooling, an oil separated which rapidly crystallized. The solid was filtered at 0°C, washed with ice water, and dried under vacuum to yield 1.608 g. (44%) of hesperetin dihydrochalcone, m.p. 118°–138.5°C. Two recrystallizations from 2:1 $H_2O$/EtOH gave analytically pure material, m.p. 142.5°–146.5°C., dec. Anal.: Calculated for $C_{16}H_{16}O_6 \cdot 1/2 H_2O$: C, 61.4; H, 5.4. Found: C, 61.19; H, 5.41.

In Step (1) of the above procedure, the isovanillin is replaced by an equivalent amount of 3-hydroxy-4-propoxybenzaldehyde and the hesperetin dihydrochalcone homolog, 3-(3-hydroxy-4-propoxyphenyl)phloropropiophenone is secured.

In Step (2) of the above procedure the α-cyano-3-hydroxy-4-methoxycinnamic acid is reduced with one equivalent of sodium borohydride in aqueous ethanol (1:1 vol.) and the desired dihydrocinnamic acid is secured.

In Step (4) of the above process the zinc chloride is replaced by an equivalent amount of zinc bromide, titanium tetrachloride and stannic chloride, respectively, with equivalent results. The HCl is replaced with HBr, with equivalent results.

Sweetener Compositions

As in the case of the dihydrochalcone sweeteners (see the copending applications of Rizzi and Rizzi and Neely, above) 3-(m-hydroxyphenyl)phloropropiophenone is not substantially water-soluble but exhibits its sweetener properties when properly dissolved. Once dissolved, in conjunction with various solvents, natural oils and the like, it is suitable for use as artificial sweetener compositions and to enhance the natural sweetness of certain poly-ols and sugars. Therefore, the sweetener compositions of this invention comprise 3-(m-hydroxyphenyl)phloropropiophenone dissolved in certain solvents as hereinafter defined. In its method aspects, this invention comprises a method for potentiating the sweetness of certain sugars and poly-ols, and a method for sweetening foods, beverages, dentifrices, chewing gums, mouthwashes and other ingestible compositions.

Suitable solvents for the sweetener compositions containing 3-(m-hydroxyphenyl)phloropropiophenone include the group consisting of ingestible, polar, organic liquids, and mixtures of said ingestible, polar, organic liquids and water containing at least about 0.15% by weight of said ingestible, polar, organic liquids. Such solvents include the members of the hereinafter disclosed classes of polar, organic liquids, especially those detailed in the list of permitted food additives periodically prepared and issued by the United States Food & Drug Administration and published in the Federal Register, and commonly referred to as the GRAS (Generally Recognized as Safe) list. Another group of ingestible organic solvents useful herein are the polar, organic liquids classified as safe for limited use in foods under the provisions of regulation 121.1164 of the U.S. Food and Drug Administration.

For example, liquid aldehydes and ketones, e.g., acetophenone, 3-decen-2-one, isopulegone and the like, all dissolve the 3-(m-hydroxyphenyl)phloropropiophenone and provide sweetener compositions.

A variety of liquid alcohols, e.g., ethyl alcohol, cedrol, 3-hexen-1-ol, neopentyl alcohol, 1-decanol, sorbitan monooleate polyoxyethylene and the like, are all suitable for use singly, in admixture one with another, and in water, to solubilize the 3-(m-hydroxyphenyl)phloropropiophenone and thereby provide artificial sweetener compositions.

The liquid organic acid esters of the formula RCOOR, wherein R represents straight-chain and branched alkyl groups having 1 to 10 carbon atoms, are a preferred class of solvents for use herein. The usefulness of such esters arises both because of their good solvent properties and by virtue of the fact that many esters are suitable for prolonged ingestion, themselves being major components of most natural flavor oils. Non-limiting examples of esters useful as ingestible, polar, organic liquid solvents herein include: pentyl pentanoate, isobutyl formate, ethyl acetate, amyl valerate, isoamyl valerate, butyl butyrate, isobutyl propionate, isoamyl decanoate, ethyl propionate, ethyl butyrate, isoamyl acetate and isobutyl valerate, all of which are suitable for use singly, in admixtures, and with water, in the sweetener compositions herein.

Low molecular weight organic acids, e.g., acetic acid and aqueous solutions thereof such as vinegar, are also suitable for use as the solvent herein.

Similarly, various naturally-occurring and synthetically-reconstituted flavor oils which are obtainable from plants are suitably employed to solubilize the 3-(m-hydroxyphenyl)-phloropropiophenone used in this invention, thereby providing sweetener compositions. It is not possible to specify with certainty the compositions of these various oils other than that they are highly complex liquid mixtures containing polar organic compounds such as lactones, ketones, aldehydes, thiols, carboxylic acids and acid esters. Some flavor oils contain nitriles, imides, organonitrates and the like. A long history of use by humans has shown that such flavor oils are physiologically acceptable and they are thus also preferred for use as ingestible organic solvents herein. Often, such flavor oils are employed with ethyl alcohol and 1,2-propylene glycol to provide various extracts, tinctures and concentrates containing said oils and it is a contemplated mode of the practice of this invention that such solutions can be used herein to provide sweetener compositions. These naturally-occurring, ingestible organic solvent oils can also be used with water and any of the above-noted preferred liquids as a co-solvent. Non-limiting examples of flavor oils suitable for use as solubilizing agents for 3-(m-hydroxyphenyl)phloropropiophenone include: oil of sweet birch, oil of spearmint, oil of wintergreen, oil of sassafras, cedar wood oil, anise oil, pine oil, dill oil, celery seed oil, various citrus oils including lemon, orange, lime, tangerine and grapefruit oils, clove oil, peppermint oil, cassia, carrot seed oil, cola concentrate, ginger oil, angelica oil and the like, singly and in admixtures, and all such oils can be used in the practice of this invention to dissolve 3-(m-hydroxyphenyl)phloropropiophenone to provide sweetener compositions. These oils are obtained from the appropriate plant sources by extraction in the manner wellknown to those skilled in the art.

Any of the above-described ingestible, polar, organic liquids can be used in conjunction with water to provide aqueous-organic solvent systems useful in the preparation of the artificial sweetener compositions herein. For example, 3-(m-hydroxyphenyl)phloropropiophenone can be dissolved in ethyl alcohol and then diluted with water to yield a 0.002 molar solution of said phloropropiophenone containing five percent ethyl alcohol, which composition is suitable for sweetening foods and beverages.

The 3-(m-hydroxyphenyl)phloropropiophenone is also suitable for enhancing the natural sweetness of certain sugars, "sugar alcohols" (i.e., the poly-ols formed by reduction of natural sugars) and glycerol. For example, co-dissolution of 3-(m-hydroxyphenyl)phloropropiophenone with sugars such as glucose, fructose, lactose, mannose and cellibiose using an organic, or, preferably a mixed aqueous-organic solvent of the type disclosed above, substantially enhances the sweetness of the sugar. In like fashion, co-dissolution of 3-(m-hydroxyphenyl)phloropropiophenone with the exemplary sugar alcohols xylitol, mannitol and sorbitol, as well as with glycerol, substantially enhances the natural sweetness of these poly-ols. Again, it is to be recognized that it is a critical aspect when using 3-(m-hydroxyphenyl)phloropropiophenone to enhance the sweetness of the various poly-ols and natural sugars, that said 3-(m-hydroxyphenyl)phloropropiophenone be co-dissolved therewith by means of any of the foregoing polar, organic liquids or water containing at least about 0.15% of said organic liquids.

Accordingly, the present invention encompasses sweetener compositions comprising from about a $5 \times 10^{-4}$ molar to about 2.0 molar, preferably about a $5 \times 10^{-1}$ to about 1.0 molar, concentration of 3-(m-hydroxyphenyl)phloropropiophenone and a solvent selected from the group consisting of ingestible, polar, organic liquids of the type hereinabove disclosed and mixtures of said ingestible, polar, organic liquids and water containing at least about 0.15% by weight of said ingestible, polar, organic liquids. Preferred ingestible polar, organic liquids useful in the compositions herein include ethyl alcohol, 1,2-dihydroxypropane, acetic acid, ethyl acetate, sorbitan monooleate polyoxyethylene, isoamyl acetate, isoamyl valerate, butyl butyrate, isobutyl propionate, as well as the natural oils such as spearmint oil, peppermint oil, cola extract, citrus oils, and the like, disclosed above, and mixtures thereof.

The present invention also encompasses sweetener compositions comprising from about 1% to about 99% by weight of a poly-ol compound of the formula $HOCH_2(CHOH)_nCH_2OH$ wherein n is an integer from 1 to 4, and 3-(m-hydroxyphenyl)phloropropiophenone codissolved at a weight ratio of poly-ol:3-(m-hydroxyphenyl)phloropropiophenone in the range from about $1:10^{-6}$ to 1:1, preferably from about $1:10^{-5}$ to about $1:10^{-3}$, in a solvent of the type hereinabove disclosed. Preferred poly-ols in said sweetener compositions include xylitol, sorbitol, mannitol and glycerol.

The present invention also encompasses sugar containing sweeteners comprising from about 2% to about 70% by weight of a natural sugar selected from the group consisting of sucrose, glucose, frutose, lactose, mannose and cellibiose and 3-(m-hydroxyphenyl)phloropropiophenone codissolved in a solvent of the type hereinabove disclosed at a weight ratio of sugar to 3-(m-hydroxyphenyl)phloropropiophenone from about $1:10^{-6}$ to about 1:1, more preferably from about $1:10^{-3}$ to about $1:10^{-1}$.

The following examples illustrate the sweetener compositions of this invention, but are not intended to be limiting thereof. In each instance, the 3-(m-hydroxyphenyl)phloropropiophenone is dissolved in the ingestible organic solvent by stirring at 30°C to 50°C. When water is used in the composition as a co-solvent, the 3-(m-hydroxyphenyl)phloropropiophenone is conveniently pre-dissolved in the organic solvent and the resulting solution is mixed with the water.

EXAMPLE III

Five grams of 3-(m-hydroxyphenyl)phloropropiophenone are dissolved in 100 g. of ethyl alcohol and 1000 g. of water is admixed therewith. The resulting solution is suitable for use as a sweetener composition without further treatment.

EXAMPLE IV

Three-fourths gram of 3-(m-hydroxyphenyl)phloropropiophenone is dissolved in 20 g. of 1,2-dihydroxypropane at 50°C. The resulting solution is suitable for use as a sweetener composition without further treatment.

EXAMPLE V

A concentrated, non-aqueous sweetener composition having an intense sweetness is prepared in the following manner: 10 g. of 3-(m-hydroxyphenyl)phloropropiophenone is dissolved in 100 g. of ethyl alcohol. The resulting solution is suitable for use as a highly concentrated sweetener composition without further treatment.

EXAMPLE VI

One-half gram of 3-(m-hydroxyphenyl)phloropropiophenone is dissolved in a mixture of 1000 g. of water and 50 g. of sorbitan monooleate polyoxyethylene with gentle warming. The resulting solution is suitable for use as a sweetener composition without further treatment.

EXAMPLE VII

One-tenth part of 3-(m-hydroxyphenyl)phloropropiophenone is dissolved in 10 parts of isoamyl acetate and the resulting solution provides a banana-flavored sweetener composition.

EXAMPLE VIII 0.2 gram of 3-(m-hydroxyphenyl)phloropropiophenone is dissolved in 100 g. of ethyl alcohol and 1000 g. of water is admixed therewith; 80 g. of sucrose is then dissolved in the solution. The sweetness of the sucrose is substantially enhanced and the resulting solution is suitable for use as a sweetener composition without further treatment.

The sucrose is replaced by an equivalent amount of fructose, glucose, lactose and cellibiose, respectively, and equivalent results are secured.

EXAMPLE IX $5 \times 10^{-6}$ mole of 3-(m-hydroxyphenyl)phloropropiophenone is dissolved in 15 ml. of a synthetic pineapple oil (corresponding to winter fruit) consisting of 2.91 parts ethyl acetate, 0.61 parts acetaldehyde, 0.45 parts methyl n-valerate, 0.60 parts methyl isovalerate, 1.40 parts methyl isocaproate and 0.75 parts methyl caprylate and thence diluted to one liter with a solution of 50 parts mannose in 100 parts water. The natural sweetness of the mannose is enhanced and a pineapple-flavored sweetener composition is provided.

EXAMPLE X

A sweetener composition having a spearmint flavor is prepared as follows: $5 \times 10^{-3}$ mole of 3-(m-hydroxyphenyl)phloropropiophenone is dissolved in 1000 ml. of water in which is dissolved 0.15% spearmint oil and a mixture of 20 g. sucrose and 20 g. fructose by heating for 10 minutes at 60°C. The sweetness of the sucrose-fructose combination is substantially enhanced.

The spearmint oil is replaced by oil of sweet birch, oil of wintergreen, oil of sassafras, cedar wood oil, anise oil, pine oil, dill oil, celery seed oil, lemon oil, lime oil, orange oil, grapefruit oil, tangerine oil, peppermint oil, clove oil, cassia, carrot seed oil, cola concentrate, ginger oil, angelica oil and mixtures thereof, respectively, and sweetener compositions of the corresponding flavors are secured.

EXAMPLE XI

One-half part of 3-(m-hydroxyphenyl)phloropropiophenone is dissolved in 10 parts bitter almond oil and the resulting solution is added to a solution of 700 parts sorbitol in 1000 parts water. The weak natural sweetness of the sorbitol is enhanced and an almond-flavored sweetener composition is provided.

The bitter almond oil is replaced by oil of sweet birch, oil of spearmint, oil of wintergreen, oil of sassafras, cedarwood oil, anise oil, pine oil, dill oil, celery seed oil, lemon oil, lime oil, orange oil, grapefruit oil, tangerine oil, peppermint oil, clove oil, cassia, carrot seed oil, cola concentrate, ginger oil and angelica oil, respectively, and sweetener compositions of the corresponding flavors are secured.

The sorbitol is replaced by an equivalent amount of xylitol, mannitol, glycerol and 1,2,3,4-tetrahydroxybutane, respectively, and equivalent results are secured.

EXAMPLE XII

Brewed coffee and tea are sweetened as follows: a sufficient volume of the sweetener composition described in Example III is added to coffee and tea, respectively, such that the final concentration of dissolved 3-(m-hydroxyphenyl)phloropropiophenone is about 0.005% by weight of the brewed beverage, or greater, according to taste.

What is claimed is:

1. A sweetener composition comprising from about a $5 \times 10^{-4}$ molar to about a 2.0 molar concentration of 3-(m-hydroxyphenyl)phloropropiophenone of the formula

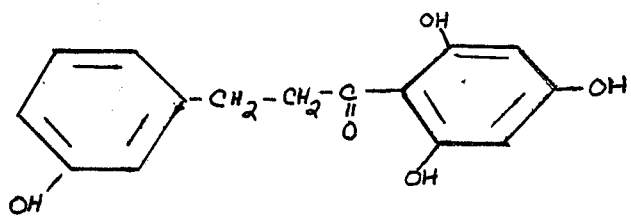

and a solvent selected from the group consisting of ingestible, polar, organic liquids, and mixtures of ingestible, polar, organic liquids and water, said mixtures containing at least about 0.15% by weight of said ingestible, polar, organic liquids.

2. A composition according to claim 1 wherein the ingestible, polar, organic liquid is a member selected from the group consisting of liquid alcohols, glycols, low molecular weight organic acids, organic acid esters, aldehydes, ketones and mixtures thereof.

3. A composition according to claim 1 wherein the ingestible, polar, organic liquid is a member selected from the group consisting of ethyl alcohol, 1,2-dihydroxypropane, acetic acid, ethyl acetate, sorbitan monooleate polyoxyethylene, isoamyl acetate, isoamyl valerate, butyl butyrate, isobutyl propionate, oil of sweet birch, oil of spearmint, oil of wintergreen, oil of sassafras, cedarwood oil, anise oil, pine oil, dill oil, celery seed oil, lemon oil, orange oil, lime oil, grapefruit oil, clove oil, peppermint oil, tangerine oil, cassia, carrot seed oil, cola concentrate, ginger oil, angelica oil and mixtures thereof.

4. A sweetener composition comprising from about 1% to about 99% of a poly-ol compound of the formula $HOCH_2(CHOH)_nCH_2OH$ wherein $n$ is an integer from 1 to 4, and 3-(m-hydroxyphenyl)phloropropiophenone of the formula

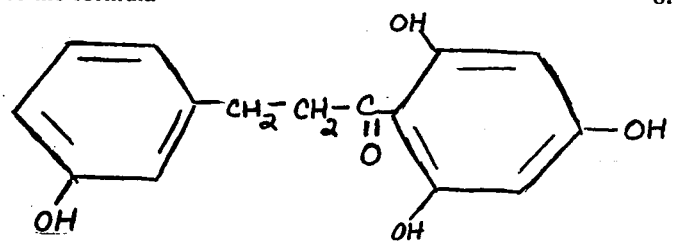

at a weight ratio of poly-ol:3-(m-hydroxyphenyl)phloropropiophenone in the range from about $1:10^{-6}$ to 1:1 dissolved in a solvent selected from the group consisting of ingestible, polar, organic liquids and mixtures of ingestible, polar, organic liquids and water, said mixtures containing at least about 0.15% by weight of said ingestible, polar, organic liquids.

5. A composition according to claim 4 wherein the poly-ol compound is selected from the group consisting of xylitol, sorbitol, mannitol and glycerol.

6. A composition according to claim 4 wherein the ingestible, polar, organic liquid is a member selected from the group consisting of ethyl alcohol, 1,2-dihydroxypropane, acetic acid, ethyl acetate, sorbitan monooleate polyoxyethylene, isoamyl acetate, isoamyl valerate, butyl butyrate, isobutyl propionate, oil of sweet birch, oil of spearmint, oil of wintergreen, oil of sassafras, cedarwood oil, anise oil, pine oil, dill oil, celery seed oil, lemon oil, orange oil, lime oil, grapefruit oil, clove oil, peppermint oil, tangerine oil, cassia, carrot seed oil, cola concentrate, ginger oil, angelica oil and mixtures thereof.

7. A sweetener composition comprising from about 2% to about 70% by weight of a natural sugar and 3-(m-hydroxyphenyl)phloropropiophenone of the formula

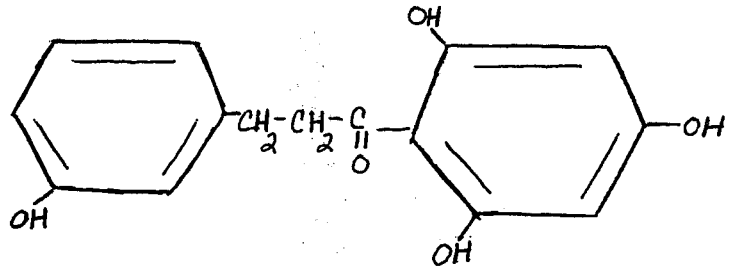

at a weight ratio of sugar:3-(m-hydroxyphenyl)phloropropiophenone in the range from about $1:10^{-6}$ to 1:1 dissolved in a solvent selected from the group consisting of ingestible, polar, organic liquids and mixtures of ingestible, polar, organic liquids and water, said mixtures containing at least about 0.15% by weight of said ingestible, polar, organic liquids.

8. A composition according to claim 7 wherein the sugar is selected from the group consisting of glucose, fructose, sucrose, lactose, mannose and cellibiose.

9. A composition according to claim 7 wherein the ingestible, polar, organic liquid is a member selected from the group consisting of ethyl alcohol, 1,2-dihydroxypropane, acetic acid, ethyl acetate, sorbitan monooleate polyoxyethylene, isoamyl acetate, isoamyl valerate, butyl butyrate, isobutyl propionate, oil of sweet birch, oil of spearmint, oil of wintergreen, oil of sassafras, cedarwood oil, anise oil, pine oil, dill oil, celery seed oil, lemon oil, orange oil, lime oil, grapefruit oil, clove oil, peppermint oil, tangerine oil, cassia, carrot seed oil, cola concentrate, ginger oil, angelica oil and mixtures thereof.

* * * * *